US010988716B2

(12) United States Patent
Fardim et al.

(10) Patent No.: US 10,988,716 B2
(45) Date of Patent: Apr. 27, 2021

(54) POLYSACCHARIDE DERIVATIVES AS OPTICAL BRIGHTENING AGENTS

(71) Applicant: Åbo Akademi University, Turku (FI)

(72) Inventors: Pedro Fardim, Turku (FI); Thomas Heinze, Jena (DE); Holger Wondraczek, Jena (DE); Olga Gabova, Turku (FI)

(73) Assignee: ABO AKADEMI UNIVERSITY, Turku (FI)

( * ) Notice: Subject to any disclaimer, the term of this patent is extended or adjusted under 35 U.S.C. 154(b) by 0 days.

(21) Appl. No.: 16/072,644

(22) PCT Filed: Mar. 21, 2017

(86) PCT No.: PCT/FI2017/050193
§ 371 (c)(1),
(2) Date: Jul. 25, 2018

(87) PCT Pub. No.: WO2017/162918
PCT Pub. Date: Sep. 28, 2017

(65) Prior Publication Data
US 2019/0002801 A1  Jan. 3, 2019

(30) Foreign Application Priority Data

Mar. 22, 2016 (FI) ..................... 20165238

(51) Int. Cl.
| | | |
|---|---|---|
| *C11D 3/42* | (2006.01) | |
| *A61K 8/73* | (2006.01) | |
| *C08B 15/06* | (2006.01) | |
| *D21H 21/30* | (2006.01) | |
| *A61Q 19/00* | (2006.01) | |
| *C11D 3/28* | (2006.01) | |
| *C11D 3/20* | (2006.01) | |
| *C11D 3/34* | (2006.01) | |
| *D21H 17/24* | (2006.01) | |
| *D21C 9/00* | (2006.01) | |
| *C08B 13/00* | (2006.01) | |
| *D21H 19/38* | (2006.01) | |

(52) U.S. Cl.
CPC ............... *C11D 3/42* (2013.01); *A61K 8/731* (2013.01); *A61Q 19/00* (2013.01); *C08B 13/00* (2013.01); *C08B 15/06* (2013.01); *C11D 3/2096* (2013.01); *C11D 3/28* (2013.01); *C11D 3/3481* (2013.01); *D21C 9/005* (2013.01); *D21H 17/24* (2013.01); *D21H 19/38* (2013.01); *D21H 21/30* (2013.01); *A61K 2800/10* (2013.01); *A61K 2800/434* (2013.01); *A61K 2800/5426* (2013.01)

(58) Field of Classification Search
CPC .......... C11D 3/42; D21H 21/30; D21H 19/38; A61K 8/731; A61K 2800/10; A61K 2800/434; A61K 2800/5426; C08B 15/06; A61Q 19/00

USPC ............................................ 514/54
See application file for complete search history.

(56) References Cited

U.S. PATENT DOCUMENTS

| | | | |
|---|---|---|---|
| 7,090,829 B2 | 8/2006 | Yalpani | |
| 9,750,827 B2 | 9/2017 | Miki et al. | |
| 9,901,636 B2 | 2/2018 | Berg et al. | |
| 2003/0198599 A1 | 10/2003 | Yalpani | |
| 2007/0094814 A1 | 5/2007 | Zelger et al. | |
| 2007/0169903 A1 | 7/2007 | Covarrubias et al. | |
| 2009/0114355 A1 | 5/2009 | Potrawa et al. | |
| 2011/0126995 A1* | 6/2011 | Turunen | D21H 17/07 162/162 |
| 2012/0238524 A1 | 9/2012 | Ritter et al. | |
| 2015/0202293 A1 | 7/2015 | Berg et al. | |
| 2015/0374856 A1 | 12/2015 | Miki et al. | |

FOREIGN PATENT DOCUMENTS

| | | |
|---|---|---|
| CN | 105061605 A | 11/2015 |
| JP | S 54126286 A | 10/1979 |
| JP | S 55161801 A | 12/1980 |
| JP | H 08100001 A | 4/1996 |
| JP | 2005531647 A | 10/2005 |
| JP | 2007099967 A | 4/2007 |
| JP | 2009524749 A | 7/2009 |
| JP | 2010275408 A | 12/2010 |
| JP | 2014185333 A | 10/2014 |
| JP | 2015516496 A | 6/2015 |
| WO | WO 2004/111330 A1 | 12/2004 |
| WO | WO 2007/087320 A2 | 8/2007 |
| WO | 2013189663 A1 | 12/2013 |

OTHER PUBLICATIONS

Tauscher et al. Synthesis and Characterization of New 4-Hydroxy-1,3-thiazoles. Synthesis 2010(10):1603-1608. DOI: 10.1055/s-0029-1219759 (Year: 2010).*
Stippich et al. Novel luminescence dyes and ligands based on 4-hydroxythiazole. Journal of Sulfur Chemistry vol. 30, No. 2, Apr. 2009, 109-118. (Year: 2009).*
Office Action dated Jun. 14, 2019, by the Japanese Patent Office in corresponding Japanese Patent Application No. 2018-544538, and an English Translation of the Office Action. (6 pages).

(Continued)

*Primary Examiner* — Yih-Horng Shiao
(74) *Attorney, Agent, or Firm* — Buchanan Ingersoll & Rooney PC

(57) ABSTRACT

Provided herein are polysaccharide derivatives substituted (a) at a degree of substitution (DS1) of at least 0.05 by a fluorescent group (FG) having a mono or polycyclic ring system including at least one heteroatom selected from N, O and S and conjugated double bonds, and having an absorption band in the UV region of light and an emission band in the visible region of light, and bonded via a first linker to any one of the native functional groups of the polysaccharide repeating units; and (b) at a degree of substitution (DS2) of at least 0.05 by a charged group (CG) bonded via a second linker to any one of the native functional groups of the polysaccharide repeating units.

37 Claims, 1 Drawing Sheet

(56) References Cited

OTHER PUBLICATIONS

International Search Report (PCT/ISA/210) dated Jul. 3, 2017, by the European Patent Office as the International Searching Authority for International Application No. PCT/FI2017/050193.
Written Opinion (PCT/ISA/237) dated Jul. 3, 2017, by the European Patent Office as the International Searching Authority for International Application No. PCT/FI2017/050193.
O. Grigoray et al., "Photoresponsive cellulose fibers by surface modification with multifunctional cellulose derivatives", Carbohydrate Polymers, 2014, pp. 280-287, vol. 111.
B. Vega et al., "Preparation of reactive fibre interfaces using multifunctional cellulose derivatives", Carbohydrate Polymers, 2015, pp. 261-273, vol. 132.
H. Wondraczek et al., "Water soluble photoactive cellulose derivatives: synthesis and characterization of mixed 2-[(4-methyl-2-oxo-2H-chromen-7-yl)oxy]acetic acid-(3-carboxypropyl)trimethylammonium chloride esters of cellulose", Cellulose, 2012, pp. 1327-1335, vol. 19.
Office Action and Search Report dated Oct. 17, 2016, by the Finnish Patent Office in corresponding Finnish Patent Application No. 20165238. (7 pages).

\* cited by examiner

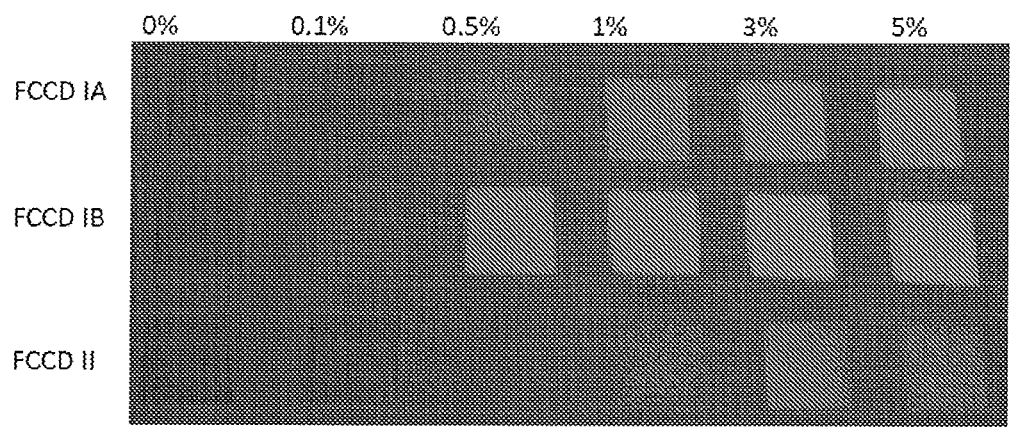

POLYSACCHARIDE DERIVATIVES AS OPTICAL BRIGHTENING AGENTS

FIELD OF THE INVENTION

The present invention relates to optical brightening agents (OBAs), and more particularly to polysaccharide-based optical brighteners.

BACKGROUND OF THE INVENTION

Stilbene derivative based optical brightening agents accounting for over 80% of all optical brightening agents (OBAs) used today are going to be banned in the near future due to a change in EU legislation. Further, ordinary OBAs have such drawbacks as instability, poor affinity to substrate, and being not easily biodegradable.

BRIEF DESCRIPTION OF THE INVENTION

It is thus an object of the present invention to provide OBAs so as to overcome the above problems. The objects of the invention are achieved by a polysaccharide derived OBAs and their uses, which are characterized by what is stated in the independent claims. The preferred embodiments of the invention are disclosed in the dependent claims.

The invention is based on the realization that incorporation of specific fluorophores and charged moieties as substituent groups in the macromolecule of polysaccharides by functionalization of the native functional groups of the polysaccharide repeating units, such as hydroxyl groups, amino groups, carboxyl groups and/or any other functional groups which may be present in the polysaccharide repeating units, by e.g. esterification or etherification reactions, provides OBAs with improved affinity to the substrate, good stability and/or biodegradability.

BRIEF DESCRIPTION OF THE DRAWINGS

In the following the invention will be described in greater detail by means of preferred embodiments with reference to the attached drawings, in which FIG. 1 shows a picture of fiber hand-sheets under black light illumination.

DETAILED DESCRIPTION OF THE INVENTION

Provided herein is polysaccharide derivatives substituted
(a) at a degree of substitution (DS1) of at least 0.05, preferably at least 0.10, by a fluorescent group (FG) comprising a mono or polycyclic ring system comprising at least one heteroatom selected from N, O and S, preferably comprising at least one nitrogen atom, and conjugated double bonds, and having an absorption band in the UV region of light and an emission band in the visible region of light, and a bonded via a first linker to any one of the native functional groups of the polysaccharide repeating units; and
(b) at a degree of substitution (DS2), of at least 0.05, preferably at least 0.10, more preferably at least 0.2, by a charged group (CG) bonded via a second linker to any one of the native functional groups of the polysaccharide repeating units.

The term "optical brightening agent (OBA)" used herein and hereafter refers to compounds also known as fluorescent whitening agents that improve the visual appearance or the optical properties such as whiteness and/or brightness of materials to which they are applied to. The fluorophores of OBAs absorb ultraviolet (UV) radiation of the incident light and emit it back as blue visible light. As a result, the materials treated with OBAs are perceived to be whiter. An optical brightening agent improves the whiteness and/or optical brightness of the material to which it is applied to as compared to the same material without the said optical brightening agent.

The term "degree of substitution (DS)" used herein and hereafter refers to the extent to which the native functional groups of the polysaccharide repeating units have been transformed by substitution with the indicated substituent groups, namely fluorescent groups (FG) and charged groups (CG). This mean value indicates the number of functionalized native functional groups in respect of the substituent group indicated.

The degree of substitution is determined by elemental analysis and may be further confirmed by other typical method used in polysaccharide analysis such as, NMR spectroscopy, FTIR spectroscopy and various other methods.

The term "native functional group" used herein and hereafter refers to substituent group of the polysaccharide core that can be subjected to ordinary synthesis methods to attach a herein defined fluorescent group (FG) or herein defined charged group (CG) to it by a covalent bond. Examples of such functional groups include hydroxyl groups, amino groups, and carboxyl groups. Preferably said native functional group is a hydroxyl group.

In the case of polyglucans the native functional groups are hydroxyl groups and the degree of substitution may be in the range from 0 to 3.

The solubility of the present polysaccharide derivatives may be adjusted by adjusting the degree of substitution in respect of both the FG and the CG. The degree of substitution (DS1) in respect of the FG affects also the perceived emitted light of the material treated with the present polysaccharide derivatives. It is further to be noted that the amount of adsorbed polysaccharide derivative has a strong effect on the emitted light. Accordingly, the degree of substitution (DS2) in respect of the CG has an effect to the affinity of the polysaccharide derivative to the substrate.

Advantageously the degree of substitution (DS1) with respect of the FG is from 0.05 to 1.50, preferably from 0.10 to 1.00, more preferably from 0.10 to 0.25.

Further advantageously the degree of substitution (DS2) with respect of CG is from 0.05 to 1.50, preferably from 0.10 to 1.50, preferably from 0.20 to 0.80, more preferably from 0.20 to 0.50.

An appropriate balance of DS1 and DS2 is adjusted to guarantee water-solubility of the polymeric OBAs.

The present polysaccharide derivative is preferably water-soluble. This has an improved effect to its adsorption to a substrate as water is a favorable medium for the interaction with the substrate. For providing water-soluble polysaccharide derivatives the degree of substitution (DS1) with respect of the FG is from 0.05 to 1.00, and the degree of substitution (DS2) with respect of CG is from 0.10 to 1.50

As discussed above both the FG and the CG are bound to the native functional groups, in particular hydroxyl groups, amino groups and/or carboxyl groups, of the polysaccharide repeating units of the polysaccharide backbone via linkers. The first and the second linker may each independently be any linker group resulting from a bond formation with a functional group being able to form a bond with a native functional group of the polysaccharide repeating units.

The first linker may for example be selected from a group consisting of —C(O)(CH$_2$)$_m$—, —C(S)(CH$_2$)$_m$—, —O(CH$_2$)$_m$—, OCH$_2$CH(OH)(CH$_2$)$_m$—, C(O)O(CH$_2$)$_m$—, C(S)O(CH$_2$)$_m$—, C(O)NH(CH$_2$)$_m$—, C(S)NH(CH$_2$)$_m$—, C(O)Ph-, C(S)Ph-, -Ph-, —C(O) OPh-, —C(S)OPh-, —C(O)NHPh-, and —C(S)NHPh-, wherein m is an integer from 1 to 6.

The second linker may for example be selected from a group consisting of —C(O)(CH$_2$)$_n$—, —C(S)(CH$_2$)$_n$—, —O(CH$_2$)$_n$—, OCH$_2$CH(OH)(CH$_2$)$_n$—, C(O)O(CH$_2$)$_n$—, C(S)O(CH$_2$)$_n$—, C(O)NH(CH$_2$)$_n$—, C(S)NH(CH$_2$)$_n$—, C(O)Ph-, C(S)Ph-, -Ph-, —C(O)OPh-, —C(S)OPh-, —C(O)NHPh-, and —C(S)NHPh-, wherein n is an integer from 1 to 6.

Preferably the first linker is —C(O)(CH$_2$)$_m$—, wherein m is an integer from 1 to 6, preferably from 1 to 4, more preferably 2 to 3.

Further preferably the second linker is —C(O)(CH$_2$)$_n$—, wherein n is an integer from 1 to 6, preferably from 2 to 4, more preferably 3.

The length of the linker chain of the first linker has an effect to the adsorption of the compounds to a substrate.

The present polysaccharide derivatives can be obtained in a manner known per se, in particular by functionalizing polysaccharides with reactive compounds thereby forming compounds of formula (I)

R$^2$—F—PS—F—R$^1$         (I)

wherein
each F is a residue of a native functional group of a repeating unit of the polysaccharide backbone;
PS is a polysaccharide backbone, with only one substituent of each substituent type shown;
R$^1$ is a fluorescent group (FG) comprising a mono or polycyclic ring system comprising at least one heteroatom selected from N, O and S and conjugated double bonds, and having an absorption band in the UV region of light and an emission band in the visible region of light, bonded via a first linker to any one of the native functional groups (F) of the polysaccharide repeating units; and
R$^2$ is a charged group (CG) bonded via a second linker to any one of the native functional groups (F) of the polysaccharide repeating units.

The present fluorescent groups (FG) comprise a mono or polycyclic ring system comprising at least one heteroatom selected from N, O and S and conjugated double bonds, and having an absorption band in the UV region of light and an emission band in the visible region of light. Advantageously the present fluorescent groups (FG) comprise at least one nitrogen atom. In addition to the preferred at least one nitrogen atom the present fluorescent groups (FG) may still further comprise one or more other heteroatoms selected from N, O and S.

In particular the present polysaccharide derivatives can be prepared by esterification of the polysaccharides with reactive compounds thereby forming compounds of formula (II)

R$^2$-O—PS—O—R$^1$         (II)

wherein
PS is a polysaccharide backbone, with only one substituent of each substituent type shown;
R$^1$ is a fluorescent group (FG) comprising a mono or polycyclic ring system comprising at least one nitrogen atom and conjugated double bonds, and having an absorption band in the UV region of light and an emission band in the visible region of light, bonded via a first linker to any one of the native hydroxyl groups of the polysaccharide repeating units; and
R$^2$ is a charged group (CG) bonded via a second linker to any one of the native hydroxyl groups of the polysaccharide repeating units.

Advantageously R$^1$ is a —C(O)(CH$_2$)$_m$— linked fluorescent group (FG), wherein m is as defined above; and R$^2$ is a —C(O)(CH$_2$)$_n$-linked charged group (CG), wherein n is as defined above.

The present charged groups (CG) may be cationic (positive charge) groups or anionic (negative charge) groups, depending on the application, e.g. the substrate to which the present polysaccharide derivative is adsorbed. The charge may originate from ionization or chemical change. For providing enhanced affinity to substrates having negative charge, e.g. wood pulp fibers, the CG is a cationic group.

In an example the native functional group (F), the CG and the second linker form a group OR$^2$ of formula (i)

—OC(O)(CH$_2$)$_n$N(R$^3$)$^+$X$^-$         (i)

wherein
n is an integer from 1 to 6, preferably from 2 to 4, more preferably 3;
each R$^3$ is independently C$_{1-6}$-alkyl, preferably C$_{1-3}$-alkyl, more preferably methyl; and
X is an anion, preferably halogen, more preferably chloride.

In an particularly advantageous example the present polysaccharide derivative is a compound of formula (II-a)

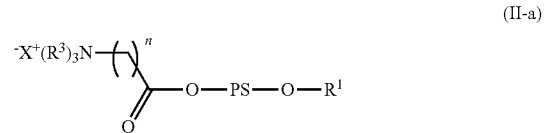

(II-a)

wherein
PS is a polysaccharide backbone, with only one substituent of each substituent type shown;
R$^1$ is a fluorescent group (FG) comprising a mono or polycyclic ring system comprising at least one nitrogen atom and conjugated double bonds, and having an absorption band in the UV region of light and an emission band in the visible region of light, bonded via a first linker to any one of the native hydroxyl groups of the polysaccharide repeating units;
each R$^3$ is independently C$_{1-6}$-alkyl, preferably C$_{1-3}$-alkyl, more preferably methyl;
n is an integer from 1 to 6, preferably from 2 to 4, more preferably 3;
and X is an anion, preferably halogen, more preferably chloride.

The present fluorescent groups (FG) comprise a mono or polycyclic ring system comprising at least one nitrogen atom and conjugated double bonds, and having an absorption band in the UV region of light and an emission band in the visible region of light. The said mono or polycyclic ring system may further comprise one or more additional heteroatom(s) each independently selected from N, O and S. The said ring system may be optionally substituted with one or more groups selected from a group consisting of aryls, e.g. phenyl, heteroaryls, e.g. pyridyl, halogen, hydroxyl, amino, nitro, cyano, C$_{1-3}$-haloalkyl, C$_{1-3}$-alkoxy, and SO$_2$.

In an advantageous example the native functional group, the FG and the first linker form a group $OR^1$ of formula (ii)

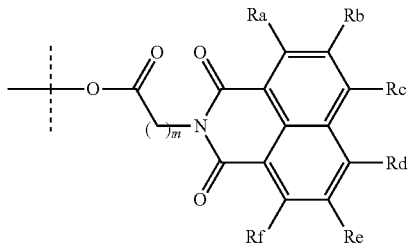
(ii)

wherein m is an integer from 1 to 6, preferably 2 to 3; and

Ra, Rb, Rc, Rd, Re, and Rf are each independently selected from a group consisting of H, halogen, hydroxyl, amino, nitro, cyano, $C_{1-3}$-haloalkyl, $C_{1-3}$-alkoxy, and $SO_2$, preferably each is selected from H or methyl, more preferably each H.

Accordingly the present polysaccharide derivative may be a compound of formula (II-b)

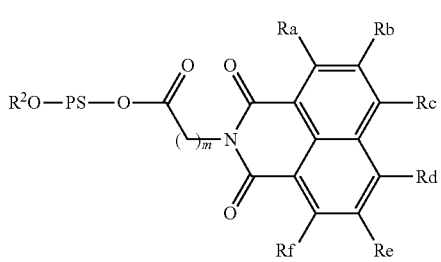
(II-b)

PS is a polysaccharide backbone, with only one substituent of each substituent type shown;

$R^2$ is a charged group (CG) bonded via a second linker to any one of the native hydroxyl groups of the polysaccharide repeating units;

m is an integer from 1 to 6, preferably 2 to 3; and

Ra, Rb, Rc, Rd, Re, and Rf are each independently selected from a group consisting of H, halogen, hydroxyl, amino, nitro, cyano, $C_{1-3}$-alkyl, $C_{1-3}$-haloalkyl, $C_{1-3}$-alkoxy, and $SO_2$, preferably each is H.

Advantageously the present polysaccharide derivative is a compound of formula (II-c)

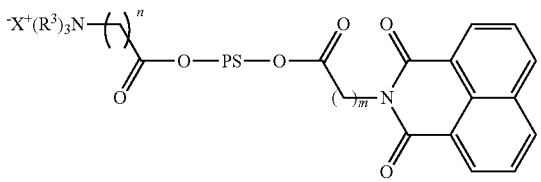
(II-c)

wherein

PS is a polysaccharide backbone, with only one substituent of each substituent type shown;

n is an integer from 1 to 6, preferably from 2 to 4, more preferably 3;

each $R^3$ is independently $C_{1-6}$-alkyl, preferably $C_{1-3}$-alkyl, more preferably methyl;

X is an anion, preferably halogen, more preferably chloride;

m is an integer from 1 to 6, preferably 2 to 3.

In another advantageous example the native functional group (F), the

FG and the first linker form a group $OR^1$ of formula (iii)

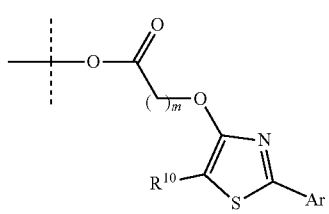
(iii)

wherein m is an integer from 1 to 6, preferably 1;

$R^{10}$ is H or $C_{1-3}$-alkyl; and

Ar is an aryl or heteroaryl, preferably pyridyl, optionally substituted one or more times with a group selected from a group consisting of halogen, hydroxyl, amino, nitro, cyano, $C_{1-3}$-haloalkyl, $C_{1-3}$-alkoxy, and $SO_2$.

Accordingly the present polysaccharide derivative may be a compound of formula (II-d)

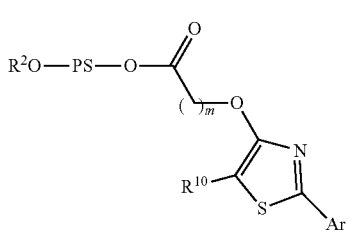
(II-d)

wherein

PS is a polysaccharide backbone, with only one substituent of each substituent type shown;

$R^2$ is a charged group (CG) bonded via a second linker to any one of the native hydroxyl groups of the polysaccharide repeating units;

m is an integer from 1 to 6, preferably 1;

$R^{10}$ is H or $C_{1-3}$-alkyl; and

Ar is an aryl or heteroaryl, preferably pyridyl, optionally substituted one or more times with a group selected from a group consisting of halogen, hydroxyl, amino, nitro, cyano, $C_{1-3}$-alkyl, $C_{1-3}$-haloalkyl, $C_{1-3}$-alkoxy, and $SO_2$.

Preferably in this example the present polysaccharide derivative is a compound of formula (II-e)

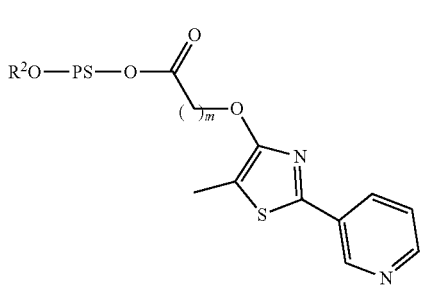
(II-e)

wherein

PS is a polysaccharide backbone, with only one substituent of each substituent type shown;

R² is a charged group (CG) bonded via a second linker to any one of the native hydroxyl groups of the polysaccharide repeating units;

m is an integer from 1 to 6, preferably 2 to 3.

Advantageously the present polysaccharide derivative is a compound of formula (II-f)

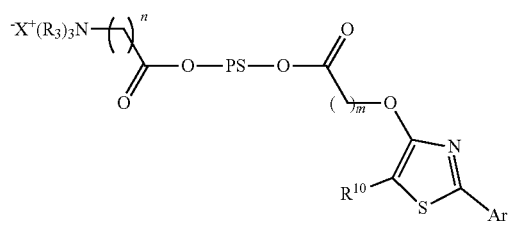

(II-f)

wherein

PS is a polysaccharide backbone, with only one substituent of each substituent type shown;

n is an integer from 1 to 6, preferably from 2 to 4, more preferably 3;

each $R^3$ is independently $C_{1-6}$-alkyl, preferably $C_{1-3}$-alkyl, more preferably methyl;

X is an anion, preferably halogen, more preferably chloride;

m is an integer from 1 to 6, preferably 1;

$R^{10}$ is H or $C_{1-3}$-alkyl; and

Ar is aryl or heteroaryl, preferably pyridyl, optionally substituted one or more times with a group selected from a group consisting of halogen, hydroxyl, amino, nitro, cyano, $C_{1-3}$-haloalkyl, $C_{1-3}$-alkoxy, and $SO_2$.

The polysaccharide backbone of the present polysaccharide derivatives is preferably derived from a polyglucan such as cellulose, hemicellulose, dextran, pullulan or starch. In one example, the polysaccharide is cellulose. In another example the polysaccharide is dextran. Use of a cellulose backbone is particularly beneficial in applications wherein the substrate comprise cellulose.

The degree of polymerization (DM), i.e. the number of monomeric repeating units, of the present polysaccharide derivatives is preferably in the range from 30 to 5000, preferred in the range from 50 to 1000, more preferred in the range from 50 to 200.

Further provided herein is use of the present polysaccharide derivatives as optical brightening agents (OBAs).

For example, the present polysaccharide derivatives can be used as OBAs in laundry detergents and/or cosmetic compositions. Accordingly provided herein is a laundry detergent comprising a present polysaccharide derivative. Further accordingly provided herein is a cosmetic composition comprising a present polysaccharide derivative.

The present polysaccharide derivatives are particularly suitable for use as OBAs in paper as they have improved affinity to fibers due to charge-directed interactions, increasing effectiveness and reducing the amount of other chemicals e.g. fixing agents and salts that would otherwise be needed for improving retention of the OBS to the fiber web.

Accordingly provided herein is a paper coating composition comprising a present polysaccharide derivative. Typically such paper coating composition further comprises at least one of a pigment and binder. Known pigments and binders may be utilized in the paper coating composition. Present polysaccharide derivatives bearing a cationic charged group (CG) are particularly beneficial for improving affinity of the compound to wood pulp fibers.

Furthermore, the present polysaccharide derivatives may be used in providing fluorescent fibers, in particular fluorescent wood pulp fibers. In particular the present polysaccharide derivatives bearing a linker bonded FG group of formula (II) are particularly suitable for this use. The fluorescent fibers may be prepared by adsorbing the present water-soluble polysaccharide derivatives to the fibers. As a result of the adsorption, the fibers gain fluorescence in the visible part of the spectrum. Thus, prepared fluorescent fibers may be used for example as authenticity indications in materials.

EXAMPLES

Step I: Addition of Fluorescent Groups to the Polysaccharide Backbone wherein at least one R1 is FG, and the other R1 are H or FG wherein at least one R1 is FG, and the other R1 are H or FG Fluorescent cellulose derivatives (FCCDs) were synthesized via reaction of cellulose with corresponding naphthalimide in the presence of N,N-carbonyldiimidazole (CDI) which acted as an activation agent. The procedure was done in the similar way as described in Wondraczek et al. *Cellulose* 2012, 19 (4), 1327-1335. Different molar ratios of anhydroglucose units (AGU) to napthalimides/CDI were used to obtain derivatives with different degree of substitution (DS) of the photoactive groups ($DS_{FG}$) ranging from 0.11 to 0.32 for N-(4-butanoic acid)-1,8-naphtalimide and from 0.07 to 0.22 for N-(3-propanoic acid)-1,8-naphtathalimide. The products of the reactions were isolated by precipitation in 2-propanol (250 mL/g of cellulose) followed by filtration, washing two times with 2-propanol (70 mL/g of cellulose) and once with water (70 mL/g of cellulose). Finally, the samples were dried under vacuum at 40° C.

Step II: Cationization of Fluorescent Polysaccharide Derivatives

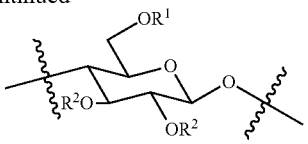

wherein at least one $R^2$ is CG, and the other $R^2$ is H or CG wherein at least one $R^2$ is CG, and the other $R^2$ is H or CG Cationization of fluorescent cellulose derivatives was done with (3-carboxypropyl)trimethylammonium chloride activated by CDI. Detailed description of the synthesis can be found in Wondraczek et al. *Cellulose* 2012, 19 (4), 1327-1335. The molar ratio of cellulose ester repeating unit (RU) to carboxylic acid/CDI was 1:0.5:0.5. DMA was used as a solvent for (3-carboxypropyl)trimethylammonium chloride and CDI.

Examples of Synthesized Derivatives

Example 1: FCCD IA

FG derived from N-(4-butanoic acid)-1,8-naphthalimide with $DS_{FG}$=0.11; CG derived from (3-carboxypropyl)trimethylammonium chloride with $DS_{CG}$=0.32.

Example 2: FCCD IB

FG derived from N-(4-butanoic acid)-1,8-naphthalimide with $DS_{FG}$=0.22; CG derived from (3-carboxypropyl)trimethylammonium chloride with $DS_{CG}$=0.33.

Example 3: FCCD II

FG derived from N-(3-propanoic acid)-1,8-naphthalimide with $DS_{FG}$=0.07; CG derived from (3-carboxypropyl)trimethylammonium chloride $DS_{CG}$=0.31.

Functionalization of Pulp Fibers

Synthesized FCCDs were used for modification of *eucalyptus* unrefined bleached Kraft pulp fibers to introduce photoactive properties to the fibers. The fiber functionalization was performed in a water-based system in one single step by addition of FCCD solutions to pulp fiber suspensions. The adsorption was conducted at mild conditions, i.e. at room temperature under agitation.

FIG. 1 shows the image of hand-sheets made of reference and modified fibers under the black light, which is commonly used to reveal counterfeiting. The UV light caused glowing of the modified fibers. The glowing effect was stronger at higher amounts of the adsorbed polymers. Visually, the difference in the optical performance between the modified fibers under the black light was in the following order: FCCD II>FCCD IA>FCCD IB. This difference was explained by the formation of excimers in the cases of FCCD IA and FCCD IB that gave additional emission band in the range of 440 nm-550 nm (blue-green region). On other hand, the sheets made of reference and modified fibers looked similar under the daylight. Hence, prepared modified fibers could serve as invisible security fibers that become visible when being exposed to UV light. One of the possible applications of such fibers is in a smart packaging. They can serve as authenticity indicator for packaging as well as for the products.

It will be obvious to a person skilled in the art that, as the technology advances, the inventive concept can be implemented in various ways. The invention and its embodiments are not limited to the examples described above but may vary within the scope of the claims.

The invention claimed is:

1. A polysaccharide derivative composition comprising a polysaccharide derivative containing substituents:
   (a) at a degree of substitution (DS1) of at least 0.05 of a fluorescent group (FG) having a mono or polycyclic ring system containing at least one heteroatom consisting of N or both N and S, and conjugated double bonds, and having an absorption band in the UV region of light and an emission band in the visible region of light, and bonded via a first linker to any one of native functional groups (F) of polysaccharide repeating units; and
   (b) at a degree of substitution (DS2) of at least 0.05 of a charged group (CG) bonded via a second linker to any one of the native functional groups of the polysaccharide repeating units.

2. The polysaccharide derivative composition as claimed in claim 1, wherein the polysaccharide derivative is a compound of formula (I):

wherein

PS is a polysaccharide backbone, with only one substituent of each substituent type shown;

each F is a native functional group of a repeating unit of the polysaccharide backbone;

$R^1$ is the fluorescent group (FG) having a mono or polycyclic ring system containing at least one heteroatom consisting of N or both N and S, and conjugated double bonds, and having the absorption band in the UV region of light and the emission band in the visible region of light, bonded via the first linker to any one of the native functional groups (F) of the polysaccharide repeating units; and $R^2$ is the charged group (CG) bonded via the second linker to any one of the native functional groups (F) of the polysaccharide repeating units.

3. The polysaccharide derivative composition as claimed in claim 1, wherein the polysaccharide derivative is a compound of formula (II):

wherein

PS is a polysaccharide backbone, with only one substituent of each substituent type shown;

$R^1$ is the fluorescent group (FG) having a mono or polycyclic ring system containing at least one nitrogen atom and conjugated double bonds, and having the absorption band in the UV region of light and the emission band in the visible region of light, bonded via the first linker to any one of native hydroxyl groups of the polysaccharide repeating units; and $R^2$ is the charged group (CG) bonded via the second linker to any one of the native hydroxyl groups of the polysaccharide-repeating units.

4. The polysaccharide derivative composition as claimed in claim 1, wherein
   the first linker is —C(O)(CH$_2$)$_m$—, wherein m is an integer from 1 to 6; and
   the second linker is —C(O)(CH$_2$)$_n$—, wherein n is an integer from 1 to 6.

5. The polysaccharide derivative composition as claimed in claim 2, wherein the CG is a cationic group.

6. The polysaccharide derivative composition as claimed in claim 5, wherein the native functional group (F), the CG and the second linker form a group $OR^2$ of formula (i):

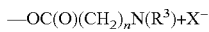

wherein n is an integer from 1 to 6;

each $R^3$ is independently $C_{1-6}$-alkyl; and

X is an anion.

7. The polysaccharide derivative composition as claimed in claim 6, wherein the polysaccharide derivative is a compound of formula (II-a):

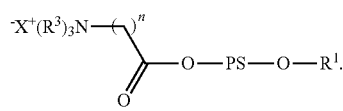

8. The polysaccharide derivative composition as claimed in claim 2, wherein the native functional group (F), the FG and the first linker form a group $OR^1$ of formula (ii):

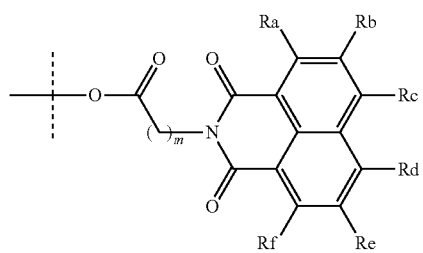

wherein m is an integer from 1 to 6; and

Ra, Rb, Rc, Rd, Re, and Rf are each independently selected from the group consisting of H, halogen, hydroxyl, amino, nitro, cyano, $C_{1-3}$-alkyl, $C_{1-3}$-haloalkyl, $C_{1-3}$-alkoxy, and $SO_2$.

9. The polysaccharide derivative composition as claimed in claim 8, wherein the polysaccharide derivative is a compound of formula (II-b):

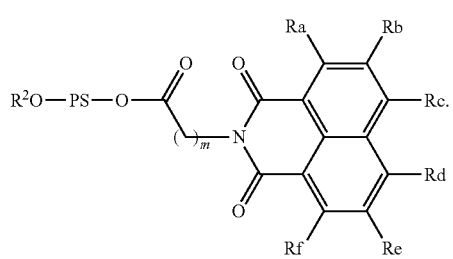

10. The polysaccharide derivative composition as claimed in claim 9, wherein the polysaccharide derivative is a compound of formula (II-c):

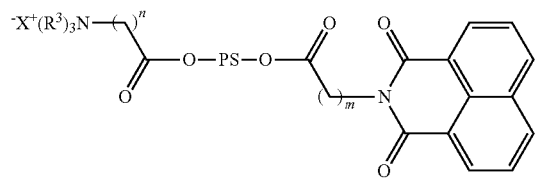

wherein

PS is a polysaccharide backbone, with only one substituent of each substituent type shown;

n is an integer from 1 to 6;

each $R^3$ is independently $C_{1-6}$-alkyl;

X is an anion; and m is an integer from 1 to 6.

11. The polysaccharide derivative composition as claimed in claim 2, wherein the native functional group (F), the FG and the first linker form a group $OR^1$ of formula (iii):

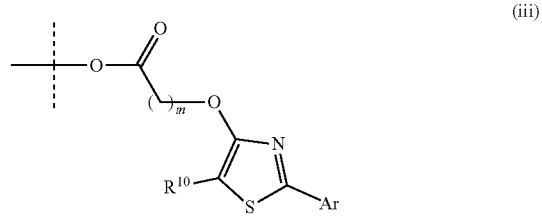

wherein m is an integer from 1 to 6; $R^{10}$ is H or $C_{1-3}$-alkyl; and

Ar is an aryl or heteroaryl, optionally containing one or more substituents selected from the group consisting of halogen, hydroxyl, amino, nitro, cyano, $C_{1-3}$-alkyl, $C_{1-3}$-haloalkyl, $C_{1-3}$-alkoxy, and $SO_2$.

12. The polysaccharide derivative composition as claimed in claim 11, wherein the polysaccharide derivative is a compound of formula (II-d):

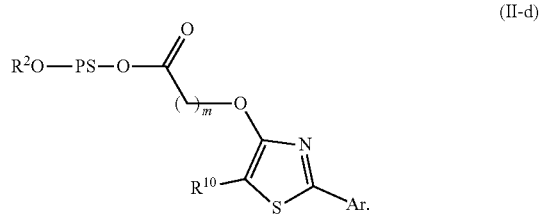

13. The polysaccharide derivative composition as claimed in claim 12, wherein the polysaccharide derivative is a compound of formula (II-f):

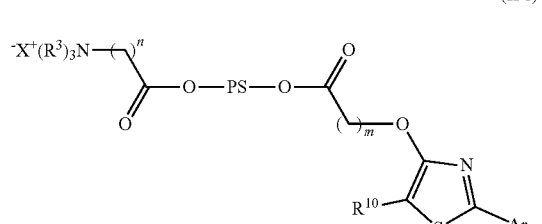

wherein

PS is a polysaccharide backbone, with only one substituent of each substituent type shown;

n is an integer from 1 to 6;

each $R^3$ is independently $C_{1-6}$-alkyl;

X is an anion;

m is an integer from 1 to 6;

$R^{10}$ is H or $C_{1-3}$-alkyl; and

Ar is aryl or heteroaryl, optionally containing one or more substituents selected from the group consisting of halogen, hydroxyl, amino, nitro, cyano, $C_{1-3}$-alkyl, $C_{1-3}$-haloalkyl, $C_{1-3}$-alkoxy, and $SO_2$.

14. The polysaccharide derivative composition as claimed in claim 1, wherein the degree of substitution (DS1) with respect of the FG is from 0.05 to 1.50.

15. The polysaccharide derivative composition as claimed in claim 1, wherein the degree of substitution (DS2) with respect of the CG is from 0.05 to 1.50.

16. The polysaccharide derivative composition as claimed in claim 1, wherein the polysaccharide is a polyglucan.

17. The polysaccharide derivative composition as claimed in claim 16, wherein the polysaccharide is cellulose.

18. The polysaccharide derivative composition as claimed in claim 16, wherein the polysaccharide is dextran.

19. A composition comprising:
a laundry detergent; and
the polysaccharide derivative composition as claimed in claim 1.

20. A composition comprising:
a cosmetic; and
the polysaccharide derivative composition as claimed in claim 1.

21. A composition comprising:
a paper coating; and
the polysaccharide derivative composition as claimed in claim 1.

22. A product comprising:
a paper; and
the polysaccharide derivative composition as claimed in claim 1.

23. A fiber product comprising:
functional fibers containing the polysaccharide derivative composition as claimed in claim 1 adsorbed therein.

24. A composition comprising:
the polysaccharide derivative composition as claimed in claim 1 as an optical brightening agent.

25. The composition as claimed in claim 24, wherein the polysaccharide derivative is an optical brightening agent in a paper product.

26. The composition as claimed in claim 24, wherein the polysaccharide derivative is an optical brightening agent in a laundry detergent.

27. The composition as claimed in claim 24, wherein the polysaccharide derivative is an optical brightening agent in a cosmetic.

28. The polysaccharide derivative composition as claimed in claim 1, wherein the at least one heteroatom is N.

29. The polysaccharide derivative composition as claimed in claim 1, wherein the at least one heteroatom is N and S.

30. The polysaccharide derivative composition as claimed in claim 1, wherein the CG is a cationic group.

31. The polysaccharide derivative composition as claimed in claim 1, wherein the native functional group (F), the CG and the second linker form a group $OR^2$ of formula (i):

wherein
n is 3;
each $R^3$ is methyl; and
X is chloride.

32. The polysaccharide derivative composition as claimed in claim 1, wherein the native functional group (F), the FG and the first linker form a group $OR^1$ of formula (ii):

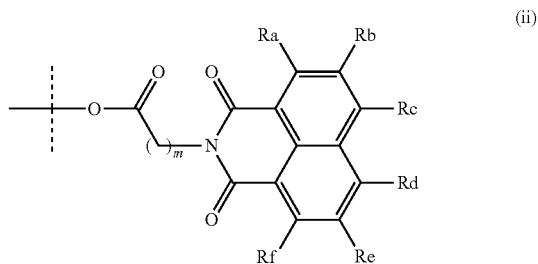

wherein
m is an integer from 2 to 3; and
Ra, Rb, Rc, Rd, Re, and Rf are each H.

33. The polysaccharide derivative composition as claimed in claim 9, wherein the polysaccharide derivative is a compound of formula (II-c):

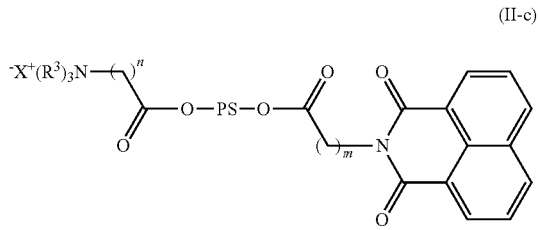

wherein

PS is a polysaccharide backbone, with only one substituent of each substituent type shown;

n is an 3;

each $R^3$ methyl;

X is chloride; and m is an integer from 2 to 3.

34. The polysaccharide derivative composition as claimed in claim 1, wherein the native functional group (F), the FG and the first linker form a group $OR^1$ of formula (iii):

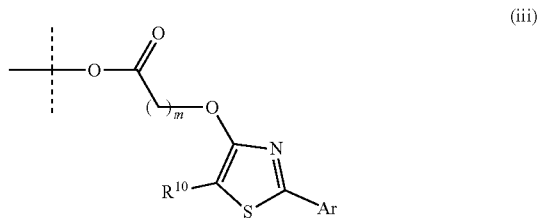

wherein
m is 1;
$R^{10}$ is H or $C_{1-3}$-alkyl; and
Ar is pyridyl, optionally containing one or more substituents selected from the group consisting of halogen, hydroxyl, amino, nitro, cyano, $C_{1-3}$-alkyl, $C_{1-3}$-haloalkyl, $C_{1-3}$-alkoxy, and $SO_2$.

35. The polysaccharide derivative composition as claimed in claim 12, wherein the polysaccharide derivative is a compound of formula (II-f):

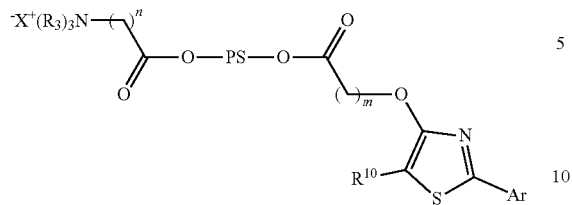
(II-f)

wherein
PS is a polysaccharide backbone, with only one substituent of each substituent type shown;
n is 3;
each $R^3$ is methyl;
X is chloride;
m is 1;
$R^{10}$ is H or $C_{1-3}$-alkyl; and
Ar is pyridyl, optionally containing one or more substituents consisting of halogen, hydroxyl, amino, nitro, cyano, $C_{1-3}$-alkyl, $C_{1-3}$-haloalkyl, $C_{1-3}$-alkoxy, and $SO_2$.

36. The polysaccharide derivative composition as claimed in claim 1, wherein the degree of substitution (DS1) with respect of the FG is from 0.10 to 0.25.

37. The polysaccharide derivative composition as claimed in claim 1, wherein the degree of substitution (DS2) with respect of the CG is from 0.20 to 0.50.

* * * * *